United States Patent
Genova et al.

Patent Number: 6,001,341
Date of Patent: Dec. 14, 1999

[54] DEODORANT AND/OR ANTIPERSPIRANT COSMETIC COMPOSITIONS

[75] Inventors: Calogero Genova, Vizzolo Predabissi; Filippo Montesion, Gropello; Edy Bozzeda, Milan; Laura Deiana, Segrate, all of Italy

[73] Assignee: Condea Augusta S.p.A., Palermo, Italy

[21] Appl. No.: 08/861,084

[22] Filed: May 21, 1997

[30] Foreign Application Priority Data

May 21, 1996 [IT] Italy .................................. MI96A1017

[51] Int. Cl.$^6$ ...................................................... A61L 9/01
[52] U.S. Cl. .................... 424/76.1; 424/76.8; 424/78.03; 424/401
[58] Field of Search .................... 424/76.1, 401, 424/76.8, 78.03

[56] References Cited

U.S. PATENT DOCUMENTS

| | | | |
|---|---|---|---|
| 4,005,189 | 1/1977 | Reese et al. | 424/47 |
| 4,675,177 | 6/1987 | Geary | 424/47 |

FOREIGN PATENT DOCUMENTS

| | | |
|---|---|---|
| 0 006 233 | 1/1980 | European Pat. Off. . |
| 2 267 757 | 11/1975 | France . |
| 2 394 290 | 1/1979 | France . |
| 24 56 639 | 6/1976 | Germany . |
| 27 21 297 | 11/1978 | Germany . |
| 43 43 264 | 6/1995 | Germany . |

*Primary Examiner*—S. Mark Clardy
*Assistant Examiner*—Kathryne E. Shelborne
*Attorney, Agent, or Firm*—Oblon, Spivak, McClelland, Maier & Neustadt, P.C.

[57] ABSTRACT

Deodorant and/or antiperspirant cosmetic compositions comprising:

(a) an alkyl ester or a mixture of alkyl esters having general formula (I):

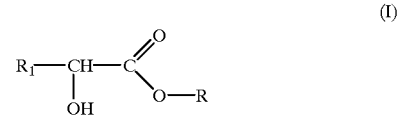

(b) one or more carrying agents.

The above compositions can be used in body deodoration of the armpits and feet and as body detergents, both for normal and sensitive subjects.

34 Claims, 1 Drawing Sheet

DEODORANT AND/OR ANTIPERSPIRANT COSMETIC COMPOSITIONS

The present invention relates to deodorant and/or antiperspirant cosmetic compositions comprising an alkyl ester or a mixture of alkyl esters.

More specifically, the present invention relates to deodorant and/or antiperspirant cosmetic compositions comprising an alkyl ester or a mixture of alkyl esters and one or more carrying agents, having a very high skin compatibility and respect for resident bacterial flora.

The above compositions can be in various physical forms such as, for example, aerosols, foams, lotions, gels, emulsions, dusting powders, suspensions, multiple phase systems, sticks, which can be packaged in various types of cosmetic containers to facilitate skin application such as, for example, aerosol or self-foaming bombs pressurized with propellants or with mechanical systems, sprays, pumps, dispensers, tubes, flasks, roll-on containers, stick containers or jars. These compositions are particularly suitable in all cases of excessive perspiration or for moderating normal perspiration, in cases of the necessity for deodoration in individuals with a sensitive skin and, in particular, in the case of individuals with skin sensitive to the traditional deodorants based on bacterial substances.

Alkyl esters such as, for example, alkyl esters of lactic, malic and tartaric acid, are lipids with a good solubility in various systems and in various cosmetic carrying agents such as, for example, hydrocarbons, triglycerides, esters, lower and higher alcohols, glycols, silicons, and have various polarities, thanks to their particular chemical structure.

In fact, alkyl esters have, in their molecular structure, a paraffinic part (the alkyl chain) and an extremely polar part represented by the ester group associated with a hydroxyl group in position $\alpha$; this chemical structure guarantees the homogeneous distribution in the hydro-lipidic film of the stratum corneum and adhesion to the surface keratin structures of the skin. In addition, their relatively easy hydrolysis produces fatty alcohols and lactic acid, the latter capable of inihibiting bacterial proliferation and the action of lipases which decompose the surface sebum forming volatile, badly-smelling, short-chain compounds. As already mentioned above, thanks to their easy solubility in various systems and in various cosmetic carrying agents, they can be easily distributed homogeneously on the skin by means of numerous carriers, without creating insolubilization phenomena after their progressive disappearance by skin absorption or volatilization of the components of the cosmetic carrier used.

Body odour is an intrinsic characteristic of human beings, due to their kind, race, family of origin, linked to behavioural habits such as food, smoking, lifestyle, work and pleasure environments, personal hygiene.

Body odour is mostly due to a combination of secretions of various glands of the skin surface, apocrines and ecrines, which secrete aqueous liquids and fatty fluids. These secretions are practically odourless when they reach the surface of the skin but, in a short time, they are decomposed by bacterial flora, creating short chain, volatile compounds, fatty acids and aldehydes having an unpleasant odour.

In modern society, body odour must be disguised as it causes an unpleasant impact on others and is considered as a sign of poor hygiene. In addition, it is made worse by clothes which often prevent the normal evaporation of the volatile compounds in an imperceptible way to smell.

Cosmetic technology is trying to combat this odour in the following ways:

with bactericidal substances: the resident bacterial flora is killed thus preventing the decomposition of sweat and the formation of odour; the disadvantages of their action are the elimination of the protective effect of the resident bacterial flora and the consequent possibility of the proliferation of exogenous species, the formation of resistant stocks and the possibility of irritation and allergies as a result of the constant contact with the skin, under occluding conditions, of bactericides which are among the most frequent allergy-causing substances in cosmetics; the above phenomena are due to the facility of trans-skin absorption under the conditions of use and reactivity of the bactericidal molecules with the cellular membranes of the skin cells;

with perfumes: in this case there is a coverage action of the body odour; the disadvantages of this action are linked to the possible allergy-causing effect of the perfumes again enhanced by the occluding and extremely hydrated conditions of the armpits;

with odour-absorbing substances: these substances are capable of stably coordinating various odorous molecules around organic zinc compounds; their action, however, is incomplete and there can also be occlusions;

with enzymatic deviators: these substances are capable of inhibiting the action of lipasic enzymes on the lipids secreted from the sebaceous glands; their action, however, is temporary and strictly linked to the quantity of inhibitor present and the skin pH;

with volatile alcohols: for example, ethyl alcohol; their action, however, is temporary and can facilitate irritation on sensitive skins and also allergies due to the carrying action of the alcohols;

with astringent substances: for example, aluminium salts with strong acid anions; these substances cause reduced perspiration but are not without dermatological risks and their astringent action prevents natural perspiration of the skin, they are also not recommended on damaged skin.

The above effects are widely described in literature such as, for example, by: Pelfini O. in "cosmetics in dermatology practice: An inquiry on the use and induced side-effects", in "Journal Applied Cosmetology" (1987), Vol. 5, pages 1–36; by Melis S. and Mignini E. in "Cosmesi Dermatologica" (1987), Year 3, N° 12, pages 13–26; by Wishart J. M.: "Generalized exfoliative dermatitis due to contact with antiperspirant", in "British Journal of Clinical Practice" (1974), Vol. 28, page 264.

The Applicant has now found that it is possible to use, for cosmetic treatment linked to the inhibition of body odour, alkyl esters combined with various cosmetic carrying agents, obtaining a considerable reduction in body odour without eliminating the resident bacterial flora, thus keeping the protective defences of the organism intact and eliminating the disadvantages of traditional deodorants.

The present invention therefore relates to deodorant and/ or antiperspirant cosmetic compositions comprising:

(a) an alkyl ester or a mixture of alkyl esters having the general formula (I):

(I)

wherein:

R₁ represents $CH_3$; $CH_2COOR$ or $CHOHCOOR$;

R represents a $C_4$–$C_{20}$ alkyl group, linear or branched; an aryl group having general formula (II):

(II)

wherein R' represents a $C_4$–$C_{20}$ alkyl group, linear or branched; an alkylethoxyl group having general formula (III):

(III)

wherein R' represents a $C_4$–$C_{20}$ alkyl group, linear or branched and n is an integer or fraction between 1 and 20, extremes included;
(b) one or more carrying agents.

Compounds (a) which are preferred for the purposes of the present invention are:

a mixture of alkyl esters of lactic acid wherein, in general formula (I), R₁ represents $CH_3$ and R represents a monobranched alkyl group containing from 12 to 13 carbon atoms; for this purpose Cosmacol ELI, sold by Condea Augusta S.p.A., was used; Cosmacol ELI is obtained by the esterification of lactic acid with a mixture of monobranched $C_{12}$–$C_{13}$ primary alcohols, obtained by an oxo-alcohol process, known under the name of Isalchem 123, sold by Condea Augusta S.p.A.;

a mixture of alkyl esters of malic acid wherein, in general formula (I), R₁ represents $CH_2COOR$ and R represents a monobranched alkyl group containing from 12 to 13 carbon atoms; for this purpose Cosmacol EMI, sold by Condea Augusta S.p.A., was used; Cosmacol EMI is obtained by the esterification of malic acid with a mixture of monobranched $C_{12}$–$C_{13}$ primary alcohols, obtained by an oxo-alcohol process, known under the name of Isalchem 123, sold by Condea Augusta S.p.A.;

a mixture of alkyl esters of tartaric acid wherein, in general formula (I), R₁ represents $CHOHCOOR$ and R represents a monobranched alkyl group containing from 12 to 13 carbon atoms; for this purpose Cosmacol ETI, sold by Condea Augusta S.p.A., was used; Cosmacol ETI is obtained by the esterification of tartaric acid with a mixture of monobranched $C_{12}$–$C_{13}$ primary alcohols, obtained by an oxo-alcohol process, known under the name of Isalchem 123, sold by Condea Augusta S.p.A.

Carrying agents (b) which can be used for the purposes of the present invention are selected from:

water;

additives preserving from bacterial contamination such as, for example, paraoxybenzoates of methyl, ethyl and propyl;

additives preserving from oxidation such as, for example, butyl-hydroxyanisole, butyl-hydroxytoluol;

mono- and poly-hydroxylic alcohols such as, for example, ethyl alcohol, isopropyl alcohol, 2-ethyl hexyl alcohol, glycerine, sorbitol, diglycerol, propylene glycol, hexylene glycol, 1,3-butandiol, dipropyleneglycol, polyethyleneglycol (PEG 200, PEG 300, PEG 400);

esters of mono- and poly-hydroxylic alcohols with acids having from 2 to 26 carbon atoms such as, for example, isopropylmyristate, isopropylpalmitate, glycerylmonostearate, isostearyl-isostearate, glyceryltriacetate, propyleneglycol monolaurate, menthyl lactate;

acetals of polyol products such as, for example, dibenzylidene sorbitol acetale;

ethers of mono- and poly-hydroxylic alcohols or their mixtures such as, for example, dimethylisosorbide, di-isopropylether; polypropyleneglycol (PPG-10 cetyl ether, PPG-14 butyl ether, PPG-27 glyceryl ether);

saturated fatty acids such as, for example, stearic acid, palmitic acid, lauric acid, behenic acid, said acids totally or partially salified with strong or medium alkalis such as, for example, sodium or potassium hydroxide, triethanolamine;

hydro- or alcohol-soluble polymers such as, for example, Carbomer, polyvinylpyrrolidone, polyvinyl alcohol, cross-polymers deriving from alkylacrylates and acrylic acid, partially or totally neutralized;

celluloses or their carboxymethyl and/or hydroxyalkyl derivatives such as, for example, hydroxymethylcellulose, hydroxyethylcellulose, hydroxypropylcellulose, sodium carboxymethylcellulose, fermentation biopolysaccharides (for example, xanthan gum);

natural and modified starches such as, for example, rice starch, oat starch, aluminium-amidosulfosuccinate;

cyclo-dextrins such as, for example, β-cyclodextrin, γ-cyclodextrin;

synthesis fluid esters such as, for example, $C_6$–$C_{18}$ triglycerides, isostearylpalmitate, myristylmyristate, benzyl benzoate, diisooctyl adipate, 2-octyldodecanol, propylenecarbonate;

vegetable oils and fluid waxes such as, for example, wheat germ oil, jojoba wax, bee-wax, sweet almond oil, macadamia oil, meadowfoam oil;

volatile and non-volatile silicons such as, for example, cyclomethicones, dimethicones;

oil-soluble or oil-dispersible rheological modifiers such as, for example, pyrogenic silica, aluminium and magnesium hydroxystearate;

non-ionic, cationic and anionic surfactants such as, for example, dimethyldistearylammonium chloride, glyceryl mono- or distearates optionally ethoxylated with a number of ethylene oxide moles varying from 2 to 40, sorbitan esters of $C_{12}$–$C_{18}$ fatty acids, sorbitan ethers of $C_{12}$–$C_{18}$ fatty alcohols, sodium or potassium cetylphosphate, sodiumlaurylethersulfate, ricinolamido propyl-methyl-ammonium methylsulfate, sodium lauryl semisulfosuccinate, coccoamphoglycinate, hydrogenated soya phospholipids, sorbitanmonolaurate optionally ethoxylated with a number of ethylene oxide moles varying from 2 to 40, lauryl, cetyl, cetylstearyl and oleyl alcohol, optionally ethoxylated with a number of ethylene oxide moles varying from 2 to 40, hydrogenated castor oil ethoxylated with a number of ethylene oxide moles varying from 2 to 40, PEG 6000 distearate, Laureth 3.

The above carrying agents (b) are added, alone or mixed with each other, to the alkyl ester or mixture of alkyl esters (a), to obtain stable or extemporaneous solutions, emulsions, microemulsions, gels or suspensions.

The above emulsions, microemulsions, gels or suspensions can also be pressurized in aerosol bombs with one or more divisions to facilitate distribution in the form of fluid, micronized drops, paste or quick-breaking foam.

Other carrying agents (b) which can be used for the purposes of the present invention are talc, sodium bicarbonate, kaolin, zinc oxide, both in free and compact form. These compounds are generally used in aqueous or hydro-alcoholic solutions or suspensions, in oily solutions or suspensions, in solid sticks poured in the molten state, aerosol bombs, in dusting powders in free and compact form.

The deodorant and/or antiperspirant cosmetic compositions of the present invention can optionally contain other additives capable of giving the product the required characteristics: gel, foam, lotion, cream, stick, aerosol, multiple phase systems, no-gas spray, fluid for roll-on.

The alkyl esters or mixtures of alkyl esters having general formula (I) can be englobed or complexed, to guarantee controlled action and/or release, for example, in β-cyclodextrin, in liposomes, in microsponges, in microcapsules, etc.

The deodorant and/or antiperspirant cosmetic compositions of the present invention can also contain other additives commonly used for this type of product such as, for example, dermatologically tested perfumes, dyes, preservatives, antioxidants, antisweat agents, essential oils, buffer substances.

Although it is difficult to define an exact concentration range of the components, the deodorant and/or antiperspirant cosmetic compositions of the present invention preferably contain:

0.2%–95% by weight of an alkyl ester or mixture of alkyl esters having general formula (I);

4.9%–99.8% by weight of one or more carrying agents;

0%–30% by weight of other additives (perfumes, dyes, antioxidants, antisweat agents (for example, aluminium-zirconium tetrachlorohydroxyglycinate, chloridrol, REACH 301, REACH 501), preservatives, essential oils (for example, menthol), buffer substances).

More preferably, the deodorant and/or antiperspirant cosmetic compositions of the present invention contain:

0.5%–80% by weight of an alkyl ester or mixture of alkyl esters having general formula (I);

19.9%–99.5% by weight of one or more carrying agents;

0%–25% by weight of other additives (perfumes, dyes, antioxidants, antisweat agents (for example, aluminium-zirconium tetrachlorohydroxyglycinate, chloridrol, REACH 301, REACH 501), preservatives, essential oils (for example, menthol), buffer substances).

The deodorant and/or antiperspirant cosmetic compositions of the present invention are obtained by adequately mixing the components with the use of the conventional equipment. The mixing and dispersion methods are well-known in the cosmetic art and consequently a detailed explanation of these would be superfluous. The methods used essentially depend on the physico-chemical and applicative characteristics of the cosmetic product to be obtained, on the type of material and form of the end-packaging: some of the most commonly used methods are described in the examples below.

A further object of the present invention relates to the use of the deodorant and/or antiperspirant cosmetic compositions described above, in body deodoration, of the armpits and feet, in both normal and sensitive subjects.

The present invention also relates to the use of the deodorant and/or anti-perspirant cosmetic compositions described above, as body detergents.

Some illustrative examples are provided to give a better understanding of the present invention and for its embodiment but they should not be considered as restricting the scope of the invention in any way.

In the following examples the buffer solution is prepared by dissolving citric acid in water at a concentration of 1.5% by weight and partially neutralizing with sodium hydroxide (NaOH) up to pH 5.5 or pH 6.0.

EXAMPLE 1

Hydro-alcoholic gel with slow evaporation

A hydro-alcoholic gel with slow evaporation is prepared, having the following composition:

deionized water: up to 100;

ethyl alcohol (90°): 40;

hydroxyethylcellulose: 0.5;

Cosmacol ELI: 3;

buffer solution at pH 5.5: 40;

perfume (PCV 612—Roure): 1;

dye (Blue Patent V): 0.001.

After dispersing the hydroxyethylcellulose in deionized water, the buffer solution at pH 5.5 and the dye are added, under stirring: the stirring is continued until the complete solution of all the components is obtained.

The Cosmacol ELI and the perfume are dissolved, under stirring, in ethyl alcohol: the stirring is continued until a limpid solution is obtained. The previous solution is added to this solution, under slow stirring.

EXAMPLE 2

Hydro-alcoholic foam

A solution for hydro-alcoholic foam having the following composition is prepared:

deionized water: up to 100;

ethyl alcohol (90°): 30;

hydroxyethylcellulose: 0.5;

ethoxylated sorbitan monolaurate (20 OE): 2;

Cosmacol ELI: 3;

buffer solution at pH 6.0: 30;

perfume (Rodinolo): 2.

After dispersing the hydroxyethylcellulose in deionized water, the buffer solution at pH 6.0 is added, under stirring: the stirring is continued until the complete solution of all the components is obtained.

The ethoxylated sorbitan monolaurate, Cosmacol ELI and the perfume are dissolved, under stirring, in ethyl alcohol: the stirring is continued until a limpid solution is obtained. The previous solution is added to this solution, under slow stirring.

The solution thus obtained is subsequently put in aerosol containers with a propane-butane propellant. The content ratio is the following: propellant 5: base 95.

EXAMPLE 3

Lotion

A lotion is prepared having the following composition:

deionized water: up to 100;
dimethyl-isosorbide: 30;
Carbomer 941: 0.5;
ethoxylated cetylstearylic alcohol(20 OE): 2;
Cosmacol ELI: 3;
buffer solution at pH 6.0: 30;
perfume (Geraniolo): 0.5;
dye (CI 19120): 0.001
preservatives (Bronopol): 0.02.

After dispersing the Carbomer 941 in deionized water, the buffer solution at pH 6.0, the dye and the preservative are added, under stirring: the stirring is continued until the complete solution of all the components is obtained.

The ethoxylated cetylstearylic alcohol, Cosmacol ELI and the perfume are dissolved, under stirring, in dimethyl-isosorbide: the stirring is continued until a limpid solution is obtained. The previous solution is added to this solution, under slow stirring.

EXAMPLE 4

Lotion

A lotion is prepared having the following composition:
ethyl alcohol (95%): 58;
Cosmacol ELI: 2;
buffer solution at pH 5.5: 40.

The lotion is obtained by dissolving, at room temperature, the Cosmacol ELI in ethyl alcohol and subsequently adding the buffer solution at pH 5.5.

EXAMPLE 5

Hydro-alcoholic emulsion

A hydro-alcoholic emulsion is prepared having the following composition:
deionized water: up to 100;
ethyl alcohol (95%): 40;
Carbomer 940: 1;
ethoxylated oleylic alcohol (20 OE): 3;
Cosmacol ELI: 6;
buffer solution at pH 6.0: 30;
perfume (HBV 1242—Givadaun-Roure): 1;
dye (Red Ponceau 4R): 0.002.

The Carbomer 940 is dispersed, by means of a rapid stirrer, in deionized water: stirring is continued until the clots and swelling have completely disappeared.

The ethoxylated oleylic alcohol, Cosmacol ELI and the perfume are dissolved, under stirring, in ethyl alcohol: the stirring is continued until a limpid solution is obtained. The previous solution is added to this solution, under slow stirring: the slow stirring is continued until a homogeneous dispersion is obtained. The buffer solution at pH 6.0 and the dye are added to the dispersion thus obtained and the mixture is homogenized for 15' with a turbomixer.

EXAMPLE 6

Oily solution

An oily solution is prepared having the following composition:
isopropylmyristate: up to 100;
Cosmacol ELI: 30;
perfume (Carelia-Orissa Drebling): 2.

The above components are mixed in order, under stirring, until their complete solution is obtained. The mixture thus obtained is pressurized with propane-butane, using a mixing ratio of propellant 40: base 60, in aerosol bombs.

EXAMPLE 7

Oily solution

An oily solution is prepared having the following composition:
isopropylmyristate: up to 100;
Cosmacol EMI: 30;
perfume (Carelia-Orissa Drebling): 2.

The above components are mixed in order, under stirring, until their complete solution is obtained. The mixture thus obtained is pressurized with propane-butane, using a mixing ratio of propellant 40: base 60, in aerosol bombs.

EXAMPLE 8

Emulsion

An emulsion is prepared having the following composition:
deionized water: up to 100;
Carbomer 1342: 1;
ethoxylated sorbitan monolaurate (20 OE): 3;
Cosmacol ELI: 2;
buffer solution at pH 6.0: 30;
perfume (Pino Mugo 1342-ICSA-Florasynth): 1.

The Carbomer 1342 is dispersed in deionized water, the Cosmacol ELI is dissolved in ethoxylated sorbitan monolaurate and this solution is added to the previous solution by mixing with a turbomixer for about 10'. At the end the buffer solution at pH 6.0 is added, under slow stirring, followed by the addition of the perfume in a fine layer. The whole mixture is homogenized with a turbomixer for 5' and is then packaged in a suitable container.

EXAMPLE 9

Emulsion

An emulsion is prepared having the following composition:
deionized water: up to 100;
Carbomer 1342: 1;
ethoxylated sorbitan monolaurate (20 OE): 3;
Cosmacol ETI: 2;
buffer solution at pH 6.0: 30;
perfume (Pino Mugo 1342-ICSA-Florasynth): 1.

The Carbomer 1342 is dispersed in deionized water, the Cosmacol ETI is dissolved in ethoxylated sorbitan monolaurate and this solution is added to the previous solution by mixing with a turbomixer for about 10'. At the end the buffer solution at pH 6.0 is added, under slow stirring, followed by the addition of the perfume in a fine layer. The whole mixture is homogenized with a turbomixer for 5' and is then packaged in a suitable container.

EXAMPLE 10

Gel

A gel is prepared having the following composition:
deionized water: up to 100;
Xanthan-gum: 1;
hydrogenated soya phospholipids: 3;
Cosmacol ELI: 4;
buffer solution at pH 6.0: 30;

perfume (lavender essence France—Givadaun-Roure): 0.5;

preservative (imidazolinyl urea): 0.2.

The xanthan gum is dispersed, at room temperature, with a turbomixer, in deionized water, subsequently heating to 45° C. to obtain a viscous transluscent solution: all under stirring.

The hydrogenated soya phospholipids are dissolved in Cosmacol ELI, heating slightly to favour the solution (to about 50° C.) and, subsequently, the perfume is added. The previous solution is added to this solution, homogenizing with a turbomixer, followed by the addition of the buffer solution at pH 6.0, again homogenizing with a turbomixer. The mixture is cooled to 25° C. and the preservative is added, mixing until a complete solution is obtained.

EXAMPLE 11

Hydro-alcoholic gel

A hydro-alcoholic gel is prepared having the following composition:

deionized water: up to 100;
ethyl alcohol (95%): 40;
hydroxypropylcellulose: 0.5;
polyethylene microsponges: 2;
Cosmacol ELI: 2;
buffer solution at pH 6.0: 30;
perfume (Arabesque 0250742-Dragoco): 0.5;
preservative (phenoxyethanol): 0.5;
methyl paraoxybenzoate: 0.15.

The Cosmacol ELI, the perfume, the phenoxyethanol and the methylparaoxybenzoate are dissolved in ethyl alcohol. The hydroxypropylcellulose is dispersed in deionized water with a turbomixer and the previous solution is subsequently slowly added, mixing with a propeller stirrer.

The polyethylene microsponges and the buffer solution at pH 6.0 are then added, in order, to the homogeneous solution thus obtained, mixing with slow propeller stirring after each addition.

EXAMPLE 12

Hydro-alcoholic gel

A hydro-alcoholic gel is prepared having the following composition:

deionized water: up to 100;
ethyl alcohol (95%): 50;
hydroxyethylcellulose: 0.4;
1,3-butandiol: 2;
Cosmacol ELI: 2;
buffer solution at pH 6.0: 30;
ethoxylated hydrogenated castor oil: 2;
perfume (Green 154-FB - IFF) 1.5.

The hydroxyethylcellulose is dispersed in deionized water with a turbomixer. The 1,3-butandiol, Cosmacol ELI, ethoxylated hydrogenated castor oil and the perfume are dissolved in ethyl alcohol, mixing until a limpid solution is obtained: this solution is slowly added to the previous solution mixing with a turbomixer.

The fluid gel thus obtained can be packaged in the form of roll-on.

EXAMPLE 13

Oleolyte

An oleolyte is prepared having the following composition:

pyrogenic silica: 2;
cyclomethicone: up to 100;
aluminium-zirconium-tetrachloro-hydroxyglycinate: 20;
Cosmacol ELI: 4;
perfume (Concentrate FAP—IFF) 2.

The aluminium-zirconium-tetrachlorohydroxygly-cinate is dispersed in cyclomethicone, the pyrogenic silica is then added and the mixture is homogenized with a turbomixer. The Cosmacol ELI and the perfume are then added, in order, slowly mixing after each addition.

The product obtained can be packaged in tubes or as roll-on.

EXAMPLE 14

Hydro-alcoholic stick

A hydro-alcoholic stick is prepared having the following composition:

propylene glycol: 20;
PPG-14 butyl ether: up to 100;
ethyl alcohol (95%): 10;
sodium stearate: 7;
Cosmacol ELI: 10;
cetyl alcohol: 10;
perfume (GLF 00553—Lautier Florasynth): 2;
preservative (phenoxyethanol): 0.9.

The sodium stearate is dissolved at boiling temperature with reflux in ethyl alcohol. The polyproplyene glycol, PPG-14 butyl ether, Cosmacol ELI, cetyl alcohol, perfume and preservative are then added, in order, the temperature being maintained at about 70° C. The mixture is then poured into suitable containers for sticks and is cooled in a suitable refrigerating equipment.

EXAMPLE 15

Non-alcoholic stick

A non-alcoholic stick is prepared having the following composition:

dipropylene glycol: up to 100;
PEG 200: 20;
propylene glycol: 10;
Laureth 3: 10;
Cosmacol ELI: 5;
2-octyl dodecanol: 5;
cetylstearyl alcohol: 1;
aluminium and magnesium hydroxystearate: 10;
cyclomethicone: 30;
perfume (Fragrance 1-2-33678 —Lautier-Florasynth): 1.2;
preservative (phenoxyethanol): 0.8.

The dipropylene glycol, PEG 200, propylene glycol and Laureth 3 are mixed until a homogeneous solution is obtained and this is then heated to 60° C. The Cosmacol ELI, 2-octyl dodecanol and cetylstearyl alcohol are then added, in order, mixing until a solution is obtained after each addition and maintaining the temperature constant at 60° C.

The aluminium and magnesium hydroxystearate are then added and the whole mixture is dispersed with a turbomixer. When the dispersion is complete it is cooled to about 55° C., the cyclomethicone is then added, mixing until homogeneity is obtained and the perfume and preservative are then added, in this order, under continuous mixing.

The mixture is then poured into suitable moulds for deodorant sticks, cooling to 10° C.

EXAMPLE 16

Non-alcoholic stick

A non-alcoholic stick is prepared having the following composition:

acetal dibenzylidene sorbitol: 2;
hydroxypropylcellulose: 1;
dipropyleneglycol: up to 100;
PEG 300: 15;
propylene glycol: 10;
proylenecarbonate: 5;
deionized water: 15;
PPG-27 glyceryl ether: 1;
Cosmacol ELI: 5;
2-octyl dodecanol: 5;
perfume (Abbalide DEP—Bush, Boake and Allen): 1;
preservative (phenoxyethanol): 0.9.

The hydroxypropylcellulose is dispersed in deionized water until complete swelling takes place. A solution of acetal dibenzylidene sorbitol, dipropyleneglycol, PEG 300 and propylene glycol is prepared, it is heated to 70° C. and then the propylenecarbonate is added, under stirring. The solution of PPG 27 glyceryl ether, Cosmacol ELI, 2-octyl dodecanol, perfume and preservative, previously prepared, is added to this solution, the temperature being maintained constant at 70° C.

The dispersion of hydroxypropylcellulose in water, previously prepared, is added, in a fine layer, to the solution thus obtained and the whole mixture is poured into moulds for deodorants sticks, which are then placed in a suitable cooling plant.

EXAMPLE 17

Deodorant cream

A deodorant cream is prepared having the following composition:

glycerylmonostearate: 4;
isopropyl palmitate: 4;
cetyl alcohol: 2;
Cosmacol ELI: 5;
ethoxylated cetyl alcohol (20 OE): 2;
bee wax: 1;
deionized water: up to 100;
buffer at pH 5.5: 30;
perfume (Abbalide DEP—Bush, Boake and Allen): 1;
preservative (phenoxyethanol): 0.9.

The glycerylmonostearate, isopropylpalmitate, cetyl alcohol, Cosmacol ELI, ethoxylated cetyl alcohol and the bee wax are melted, at 75° C. and the deionized water, previously heated to 75° C., is added, emulsifying the whole mixture with a turbomixer for about 15'. The buffer solution at pH 5.5 is then added and the cooling to 30° C. is started. Once this temperature has been reached, the perfume and preservative are added and the whole mixture is homogenized for a further 5'.

EXAMPLE 18

Deodorant powder

A deodorant powder is prepared having the following composition:

talc: up to 100;
rice starch: 20;
zinc oxide: 5;
Cosmacol ELI: 3;
pyrogenic silica: 4;
perfume (Fleurie E 9519614): 1;
preservative (phenoxyethanol): 0.5.

The powders are mixed in an adequate mixer until homogeneity is obtained. A solution of Cosmacol ELI, the perfume and preservative are prepared and this solution is sprayed, with a suitable micronizer, onto the mixture of powders in movement. The mixture is sieved with a 100 mesh oscilating screen to eliminate the clots and is packaged in suitable dispensers.

EXAMPLE 19

Product for roll-on

A product for roll-on is prepared having the following composition:

deionized water up to 100;
cross-polymer acrylate/$C_{10}$–$C_{30}$ alkyl acrylate: 0.5;
hydroxyethylcellulose: 0.5;
Cosmacol ELI: 2;
ethoxylated hydrogenated castor oil (40 OE): 4;
buffer solution at pH 5.5: 30;
perfume (Soft Flavor E-9407197 -VMF): 1.5;
preservative (imidazolinyl urea): 0.2.

The hydroxyethylcellulose is dispersed in 50% of the deionized water and then the cross-polymer acrylate/$C_{10}$–$C_{30}$ alkyl acrylate is dispersed in the remaining 50%. The two homogeneous solutions are mixed and heated to 65° C.

A solution of Cosmacol ELI and ethoxylated hydrogenated castor oil is prepared and is emulsified in the previous mixture with a turbomixer for 10'. The buffer solution at pH 5.5 is then added, under slow stirring, the mixture is cooled to 30° C. and the perfume and preservative are added under slow mixing.

EXAMPLE 20

Product for foot hygiene

A product for foot hygiene is prepared having the following composition:

water: up to 100;
propylene glycol: 5;
ethoxylated cetylstearyl alcohol (20 OE): 3;
Cosmacol ELI: 4;
"meadowfoam oil": 10;
buffer solution at pH 5.5: 30;
menthyl lactate: 1;
menthol: 0.1.

The ethoxylated cetylstearyl alcohol, Cosmacol ELI and the "meadowfoam oil" are melted, at 75° C. and the mixture of deionized water and propylene glycol, previously heated to 75° C., are added: this mixture is added, under vigorous stirring in a turbomixer, to the molten oils. After about 15' the buffer solution is added, mixing with a propeller, the mixture is cooled to 30° C., under constant stirring, and the solution of menthol in menthyl lactate previously prepared is added. Mixing is continued for a further 5' and the mixture is then discharged.

EXAMPLE 21

Deodorant stick

A deodorant stick is prepared having the following composition:

cyclomethicone: up to 100;
propylene glycol: 6;
sodium stearate: 10;
PEG 400: 9;
Cosmacol ELI: 20;
"meadowfoam oil": 20;
PPG-10 cetyl ether: 10;
ethyl alcohol (99%): 10;
perfume (Hedione—Firmenich): 0.3;
dye (cupreous chlorophylline): 0.01;
preservative (phenoxyethanol): 0.9.

The sodium stearate is dissolved in the mixture of polypropylene glycol, plus ethyl alcohol, plus PEG 400; the mixture of Cosmacol ELI, "meadowfoam oil", PPG-10 cetyl ether is heated to 70° C. and is added to the alcohol solution previously prepared, the temperature being maintained at 65° C. The cyclomethicone, dye and preservative are added, the mixture is poured into containers for deodorant sticks and is cooled in a suitable refrigerating plant.

EXAMPLE 22

Body detergent with deodorant effect

A body detergent with a deodorant effect is prepared having the following composition:

deionized water: up to 100;
sodiumlaurylethersulfate (at 70%): 25;
ethoxylated mono-jiglycerides (40 OE): 15;
ricinoleamido propyl-methyl-ammonium methylsulfate (at 30%): 2;
Cosmacol ELI: 5;
perfume (PSM 5522—Givaudan-Roure): 2;
dye (caramel): 0.4;
preservative (Bronopol): 0.015;
buffer (lactic acid or sodium lactate): up to pH 5.5–6.0.

The sodiumlaurylethersulfate, ethoxylated monodiglycerides heated to 50° C., ricinoleamido propylmethylammonium methylsulfate and Cosmacol ELI are added, in order, to the deionized water, under slow mixing until homogeneity is obtained after each addition. The perfume, dye and preservative are then added, in order, under slow mixing. The pH is adjusted with additions of the buffer (lactic acid or sodium lactate), until a pH of 5.5 or 6.0 is reached.

EXAMPLE 23

Body detergent with a deodorant effect

A body detergent with a deodorant effect is prepared having the following composition:

deionized water: up to 100;
sodium lauryl semisulfosuccinate (at 40%): 25;
coccoamphoglycinate (at 35%): 10;
PEG 6000 distearate: 15;
ethoxylated sorbitan monolaurate (20 OE): 13;
Cosmacol ELI: 10;
perfume (HBV 988—Givaudan-Roure): 2;
dye (β-carotene): 0.3;
preservative (Bronopol): 0.015;
buffer (lactic acid or sodium lactate): up to pH 5.5–6.0.

The sodium lauryl semisulfosuccinate, the coccoamphoglycinate and ethoxylated sorbitan monolaurate are dissolved in deionized water mixing slowly until homogeneity is obtained. The Cosmacol ELI is incorporated and then the PEG 6000 distearate previously melted at 70° C. is slowly added in a fine layer. The mixing is continued until homogeneity is obtained and then the perfume, dye and preservative are added, in order, the pH being adjusted to 5.5–6.0, with additions of buffer (lactic acid or sodium lactate).

EXAMPLE 24

Evaluation of efficiency

The deodorant efficiency of the lotion prepared in Example 4 was evaluated, as an example, by clinical testing on 20 volonteers.

The lotion of Example 4 is compared with an indentical lotion in which, however, the Cosmacol ELI, is substituted with a traditional bactericide: Irgasan DP 300 sold by Ciba Geigy, at 0.25%.

The subjects were preconditioned for a week, during which they did not use deodorant products or antibacterial soaps; they were then subjected to sniff tests to select the subjects with an intermediate odour level.

The subjects then used the two products for two weeks and were then subjected again to the sniff-test after 6 hours and 24 hours from the last treatment.

The armpit odour is evaluated by the use of a trained panel of sniff evaluators whereas, after the odour test, bacteria are also taken from a pre-established skin area.

BRIEF DESCRIPTION OF DRAWINGS

Figure 1:
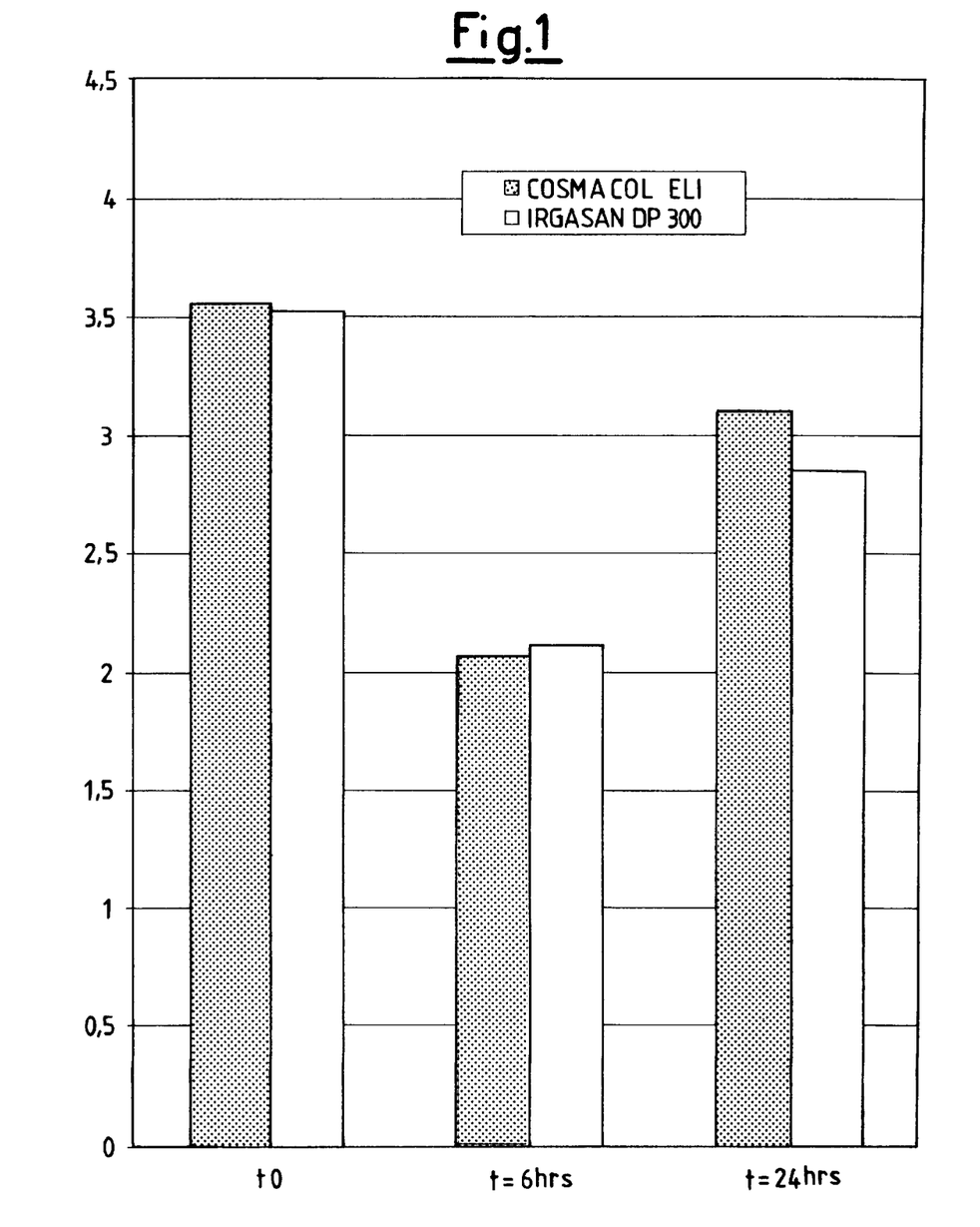

Although it does not contain bactericides, the lotion based on Cosmacol ELI has a deodorant activity after 6 and 24 hours, comparable to that of the lotion based on Irgasan DP 300, as shown in FIG. 1 (in abscissa there are the evaluation times at 0, 6 and 24 hours; in the ordinate are the average evaluation values of the sniff-test). In addition, the lotion based on Cosmacol ELI caused neither increases nor reductions in the surface bacterial flora, thus respecting the physiological equilibrium of the skin, whereas the product based on Irgasan DP 300 shows a considerable decrease in the bacterial charge.

There was no sign of irritation or intolerance in the subjects who had used the product based on Cosmacol ELI.

We claim:

1. Deodorant and/or antiperspirant cosmetic compositions consisting essentially of:
   (a) an alkyl ester or a mixture of alkyl esters having the general formula (I):

(I)

wherein:
   $R_1$ represents $CH_3$; $CH_2COOR$ or $CHOHCOOR$;
   R represents a $C_{12}$–$C_{20}$ alkyl group, linear or branched;
   an aryl group having general formula (II):

wherein R' represents a $C_4$–$C_{20}$ alkyl group, linear or branched; an alkylethoxyl group having general formula (III):

wherein R" represents a $C_4$–$C_{20}$ alkyl group, linear or branched and n is an integer or fraction between 1 and 20, extremes included;

(b) one or more carrying agents.

2. The deodorant and/or antiperspirant cosmetic compositions according to claim 1, wherein (a) is a mixture of alkyl esters of lactic acid wherein, in general formula (I), $R_1$ represents $CH_3$ and R represents a monobranched alkyl group containing from 12 to 13 carbon atoms.

3. The deodorant and/or antiperspirant cosmetic compositions according to claim 1, wherein (a) is a mixture of alkyl esters of malic acid wherein, in general formula (I), $R_1$ represents $CH_2COOR$ and R represents a monobranched alkyl group containing from 12 to 13 carbon atoms.

4. The deodorant and/or antiperspirant cosmetic compositions according to claim 1, wherein (a) is a mixture of alkyl esters of tartaric acid wherein, in general formula (I), $R_1$ represents CHOHCOOR and R represents a monobranched alkyl group containing from 12 to 13 carbon atoms.

5. The deodorant and/or antiperspirant cosmetic compositions according to claim 1, wherein the carrying agents (b) are selected from the group consisting of:

water;
additives preserving from bacterial contamination;
additives preserving from oxidation;
mono- and poly-hydroxylic alcohols;
esters of mono- and poly-hydroxylic alcohols with acids having from 2 to 26 carbon atoms;
acetals;
ethers of mono- and poly-hydroxylic alcohols or their mixtures;
saturated fatty acids;
hydro- or alcohol-soluble polymers;
celluloses or their carboxymethyl and/or hydroxyalkyl derivatives;
natural and modified starches;
cyclo-dextrins;
synthesis fluid esters;
vegetable oils and fluid waxes;
volatile and non-volatile silicons;
oil-soluble or oil-dispersible rheological modifiers;
non-ionic, cationic and anionic surfactants.

6. The deodorant and/or antiperspirant cosmetic compositions according to claim 5, wherein the additives preserving from bacterial contamination are selected from the group consisting of paraoxybenzoates of methyl, ethyl and propyl.

7. The deodorant and/or antiperspirant cosmetic compositions according to claim 5, wherein the additives preserving from oxidation are selected from the group consisting of butyl-hydroxyanisole and butyl-hydroxytoluol.

8. The deodorant and/or antiperspirant cosmetic compositions according to claim 5, wherein the mono- and polyhydroxylic alcohols are selected from the group consisting of ethyl alcohol, isopropyl alcohol, 2-ethyl hexyl alcohol, glycerine, sorbitol, diglycerol, propylene glycol, hexylene glycol, 1,3-butandiol, dipropyleneglycol and polyethyleneglycol (PEG 200, PEG 300, PEG 400).

9. The deodorant and/or antiperspirant cosmetic compositions according to claim 5, wherein the esters of mono- and poly-hydroxylic alcohols with acids having from 2 to 26 carbon atoms are selected from the group consisting of isopropylmyristate, isopropylpalmitate, glycerylmonostearate, isostearyl-isostearate, glyceryltriacetate, propyleneglycol monolaurate and menthyl lactate.

10. The deodorant and/or antiperspirant cosmetic compositions according to claim 5, wherein the acetal is dibenzylidene sorbitol acetal.

11. The deodorant and/or antiperspirant cosmetic compositions according to claim 5, wherein the ethers of mono- and poly-hydroxylic alcohols or their mixtures are selected from the group consisting of dimethyl-isosorbide, di-isopropylether and polypropyleneglycol (PPG-10 cetyl ether, PPG-14 butyl ether, PPG-27 glyceryl ether).

12. The deodorant and/or antiperspirant cosmetic compositions according to claim 5, wherein the saturated fatty acids are selected from the group consisting of stearic acid, palmitic acid, lauric acid and behenic acid, said acids totally or partially salified with strong or medium alkalis.

13. The deodorant and/or antiperspirant cosmetic compositions according to claim 5, wherein the hydro- or alcoholsoluble polymers are selected from the group of consisting of Carbomer, polyvinylpyrrolidone, polyvinyl alcohol, cross-polymers deriving from alkylacrylates and acrylic acid, partially or totally neutralized.

14. The deodorant and/or antiperspirant cosmetic compositions according to claim 5, wherein the celluloses or their carboxymethyl and/or hydroxyalkyl derivatives are selected from the group consisting of hydroxymethylcellulose, hydroxyethylcellulose, hydroxypropylcellulose, sodium carboxymethylcellulose and fermentation biopolysaccharides (xanthan gum).

15. The deodorant and/or antiperspirant cosmetic compositions according to claim 5, wherein the natural and modified starches are selected from the group consisting of rice starch, oat starch and aluminium-amido-sulfosuccinate.

16. The deodorant and/or antiperspirant cosmetic compositions according to claim 5, wherein the cyclo-dextrins are selected from the group consisting of β-cyclodextrin and γ-cyclodextrin.

17. The deodorant and/or antiperspirant cosmetic compositions according to claim 5, wherein the synthesis fluid esters are selected from the group consisting of $C_6$–$C_{18}$ triglycerides, isostearylpalmitate, myristylmyristate, benzyl benzoate, diisooctyl adipate, 2-octyldodecanol and propylenecarbonate.

18. The deodorant and/or antiperspirant cosmetic compositions according to claim 5, wherein the vegetable oils and fluid waxes are selected from the group consisting of wheat germ oil, jojoba wax, bee-wax, sweet almond oil, macadamia oil and meadowfoam oil.

19. The deodorant and/or antiperspirant cosmetic compositions according to claim 5, wherein the volatile and non-volatile silicons are selected from the group consisting of cyclomethicones and dimethicones.

20. The deodorant and/or antiperspirant cosmetic compositions according to claim 5, wherein the oil-soluble or oil-dispersible rheological modifiers are selected from the group consisting of pyrogenic silica, aluminium and magnesium hydroxystearate.

21. The deodorant and/or antiperspirant cosmetic compositions according to claim 5, wherein the non-ionic, cationic and anionic surfactants are selected from the group consisting of dimethyl-distearylammonium chloride, glyceryl mono- or distearates optionally ethoxylated with a number of ethylene oxide moles varying from 2 to 40, sorbitan esters of $C_{12}$–$C_{18}$ fatty acids, sorbitan ethers of $C_{12}$–$C_{18}$ fatty alcohols, sodium or potassium cetylphosphate, sodiumlaurylethersulfate, ricinolamido propyl-methyl-ammonium methylsulfate, sodium lauryl semisulfosuccinate, coccoamphoglycinate, hydrogenated soya phospholipids, sorbitanmonolaurate optionally ethoxylated with a number of ethylene oxide moles varying from 2 to 40, lauryl, cetyl, cetylstearyl and oleyl alcohol, optionally ethoxylated with a number of ethylene oxide moles varying from 2 to 40, hydrogenated castor oil ethoxylated with a number of ethylene oxide moles varying from 2 to 40, PEG 6000 distearate, and Laureth 3.

22. The deodorant and/or antiperspirant cosmetic compositions according to claim 1, wherein the carrying agents (b) are talc, sodium bicarbonate, kaolin, or zinc oxide, both in free and compact form.

23. The deodorant and/or antiperspirant cosmetic compositions according to claim 22, wherein the talc, sodium bicarbonate, kaolin, zinc oxide, are used in water or hydroalcoholic solutions or suspensions, in oily solutions or suspensions, solid sticks poured in the molten state, aerosol bombs or dusting powders in free and compact form.

24. The deodorant and/or antiperspirant cosmetic compositions according to claim 1, wherein other additives are present capable of giving the product the required characteristics: gel, foam, lotion, cream, stick, aerosol, multiple phase systems, no-gas spray, or fluid for roll-on.

25. The deodorant and/or antiperspirant cosmetic compositions according to claim 1 further containing dermatologically tested perfumes, dyes, preservatives, antioxidants, essential oils a buffer substances.

26. The deodorant and/or antiperspirant cosmetic compositions according to claim 1, wherein the alkyl esters or mixtures of alkyl esters having general formula (1), are englobed or complexed in β-cyclodextins, in liposomes, in microsponges or in microcapsules.

27. The deodorant and/or antiperspirant cosmetic compositions according to claim 1, wherein the carrying agents (b) are added, alone or mixed with each other, to the alkyl ester or mixture of alkyl esters (a), to obtain stable or extemporaneous solutions, emulsions, microemulsions, gels or suspensions.

28. The deodorant and/or antiperspirant cosmetic compositions according to claim 27, wherein said emulsions, microemulsions, gels or suspensions are pressurized in aerosol bombs with one or more divisions to facilitate distribution in the form of fluid, micronized drops, paste or quick-breaking foam.

29. Deodorant and/or antiperspirant cosmetic compositions consisting essentially of:
   0.2%–95% by weight of an alkyl ester or mixture of alkyl esters having general formula (1) as defined in claim 1;
   4.9%–99.8% by weight of one or more carrying agents;
   0%–30% by weight of perfumes, dyes, antioxidants, preservatives, essential oils or buffer substances.

30. Deodorant and/or antiperspirant cosmetic compositions according to claim 29, comprising:
   0.5%–80% by weight of an alkyl ester or mixture of alkyl esters having general formula (I);
   19.9%–99.5% by weight of one or more carrying agents;
   0%–25% by weight of perfumes, dyes, antioxidants, preservatives, essential oils or buffer substances.

31. The deodorant and/or antiperspirant according to claim 12, wherein the alkalis are of sodium, potassium or triethanol amine.

32. A method for body deodoration of armpits and feet in both normal and sensitive subjects, comprising applying to said armpits and feet a deodorant effective amount of the composition of claim 1.

33. A method comprising applying to a subject the composition of claim 1 in an amount effective as a body detergent.

34. The deodorant and/or antiperspirant composition according to claim 1, consisting of defined components (a) and (b).

* * * * *